US009827323B2

(12) United States Patent
Harris et al.

(10) Patent No.: US 9,827,323 B2
(45) Date of Patent: Nov. 28, 2017

(54) CONJUGATED POLYMERIC MATERIAL AND USES THEREOF

(75) Inventors: Anthony Harris, Columbia, MO (US); Johnathan Thompson, Cincinnati, OH (US); Rebecca Rone, Columbia, MO (US); Sheila Grant, Columbia, MO (US); David Grant, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 444 days.

(21) Appl. No.: 13/155,111

(22) Filed: Jun. 7, 2011

(65) Prior Publication Data

US 2012/0070466 A1 Mar. 22, 2012

Related U.S. Application Data

(60) Provisional application No. 61/397,100, filed on Jun. 7, 2010.

(51) Int. Cl.
*A61K 9/14* (2006.01)
*C07K 1/113* (2006.01)
(Continued)

(52) U.S. Cl.
CPC ............... *A61K 47/42* (2013.01); *A61K 8/02* (2013.01); *A61K 8/0241* (2013.01); *A61K 8/19* (2013.01); *A61K 8/65* (2013.01); *A61K 49/1833* (2013.01); *A61K 49/1866* (2013.01); *A61L 27/047* (2013.01); *A61L 27/24* (2013.01); *A61L 27/446* (2013.01); *A61L 27/60* (2013.01); *A61Q 19/00* (2013.01); *A61Q 19/08* (2013.01); *A61K 2800/413* (2013.01); *A61K 2800/624* (2013.01); *A61L 2400/12* (2013.01); *A61L 2400/16* (2013.01); *A61L 2430/34* (2013.01)

(58) Field of Classification Search
None
See application file for complete search history.

(56) References Cited

U.S. PATENT DOCUMENTS

| 4,582,640 A | 4/1986 | Smestad et al. ............... 530/356 |
| 6,311,690 B1 | 11/2001 | Jefferies ......................... 128/898 |

(Continued)

FOREIGN PATENT DOCUMENTS

| WO | WO 2010/033860 | 3/2010 |
| WO | WO 2010042555 A2 * | 4/2010 |

OTHER PUBLICATIONS

Castaneda et al., Collagen Cross-Linking with Au Nanoparticles, Biomacromolecules 9 (2008) 3383-3388 (Castaneda).*

(Continued)

*Primary Examiner* — Bethany Barham
*Assistant Examiner* — Dominic Lazaro
(74) *Attorney, Agent, or Firm* — Norton Rose Fulbright US LLP

(57) ABSTRACT

Disclosed are compositions comprising collagen covalently bound to particles, wherein covalent bonds are formed between reactive groups of the collagen and reactive groups of the particles, and wherein the particles have an average particle diameter ranging from 20 to 1000 nanometers. Also disclosed are various methods that utilize the compositions.

28 Claims, 8 Drawing Sheets

(51) Int. Cl.
| | |
|---|---|
| A61P 17/00 | (2006.01) |
| C12N 5/071 | (2010.01) |
| C12N 5/074 | (2010.01) |
| C12N 5/079 | (2010.01) |
| A61P 19/00 | (2006.01) |
| A61K 38/39 | (2006.01) |
| C12N 5/0735 | (2010.01) |
| B82Y 5/00 | (2011.01) |
| A61K 47/42 | (2017.01) |
| A61K 8/02 | (2006.01) |
| A61K 8/19 | (2006.01) |
| A61K 8/65 | (2006.01) |
| A61K 49/18 | (2006.01) |
| A61L 27/04 | (2006.01) |
| A61L 27/24 | (2006.01) |
| A61L 27/44 | (2006.01) |
| A61L 27/60 | (2006.01) |
| A61Q 19/00 | (2006.01) |
| A61Q 19/08 | (2006.01) |

(56) References Cited

U.S. PATENT DOCUMENTS

| | | | | |
|---|---|---|---|---|
| 6,916,909 | B1 | 7/2005 | Nicolas et al. | 530/356 |
| 2002/0128722 | A1 | 9/2002 | Jefferies | 623/23.51 |
| 2006/0257377 | A1* | 11/2006 | Atala et al. | 424/93.7 |
| 2007/0264265 | A1* | 11/2007 | Goldenberg et al. | 424/160.1 |
| 2008/0287342 | A1 | 11/2008 | Yu et al. | 514/1.1 |

OTHER PUBLICATIONS

Bellino et al., Adsorption kinetics of charged thiols on gold nanoparticles, Phys. Chem. Chem. Phys., 6 (2004) 424-428 (Bellino).*

Duan et al., Crosslinking of collagen with dendrimers, J. Biomed. Mater. Res., Part A, 75 (2005) 510-518 (Duan).*

Castaneda et al., Collagen Cross-Linking with Au Nanoparticles, Biomacromolecules 9 (2008) 3383-3388.*

Bellino et al., Adsorption kinetics of charged thiols on gold nanoparticles, Phys. Chem. Chem. Phys., 6 (2004) 424-428.*

Aillon et al., "Effects of nanomaterial physicochemical properties on in vivo toxicity," *Advanced Drug Delivery Reviews*, 61:457-466, 2009.

Billiar et al., "Effects of carbodiimide crosslinking conditions on the physical properties of laminated intestinal submocosa," *J. Biomed. Mater. Res.*, 56:101-108, 2001.

Castaneda et al., "Collagen cross-linking with Au nanoparticles," *Biomacromolecules*, 9:3383-3388, 2008.

Chan et al., "Photochemical repair of Achilles tendon rupture in a rat model," *J. Sur. Res.*, 124:274-279, 2005.

Fratzyl, Ed., *Collagen: Structure and Mechanics*, 2008.

Duan and Sheardown, "Crosslinking of collagen with dendrimers," *J Biomedical Materials Research Part A*, 75A(3):510-518, 2005.

Gratzer et al., "Control of pH alters the type of crosslinking produced by 1-ethyl-3-(3-dimethylaminopropyl)-carbodiimide (EDC) treatment of acellular matrix vascular grafts," 58:172-179, 2001.

Haidekker et al., "Influence of gold nanoparticles on collagen fibril morphology quantified using transmission electron microscopy and image analysis," *BMC Med. Imaging*, 6:4, 2006.

International Search Report and Written Opinion, issued in International Patent Application No. PCT/US2011/039497, mailed Sep. 6, 2011.

Lee et al., "The effects of crosslinking of collagen-glycosaminoglycan scaffolds on compressive stiffness, chondrocyte-mediated contraction, proliferation and biosynthesis," *Biomaterials*, 22:3145-3154, 2001.

Pieper et al., "Preparation and characterization of porous cross-linked collagenous matrices containing bioavailable chondroitin sulphate," *Biomaterials*, 20:847-858, 1999.

Rault et al., "Evaluation of different chemical methods for crosslinking collagen gel, films and sponges," *J Materials Science: Materials in Medicine*, 7(4):215-221, 1996.

Shanmugam et al., A novel single step chemical route for noble metal nanoparticles embedded organic-inorganic composite films, *Materials Chemistry and Physics*, 95:51-55, 2006.

Thomas, "The determination of log normal particle size distributions by dynamic light scattering," *Journal of Colloid and Interface Science*, 117(1):187-192, 1987.

International Preliminary Report on Patentability issued in PCT Application No. PCT/US2011/039497 dated Aug. 24, 2012.

Office Communication issued in Chinese Patent Application No. 2011800287260, dated Feb. 8, 2014.

Christensen, L. "Normal and Pathological Tissue Reactions to Soft Tissue Gel Fillers," *Dematol. Sug.* 2007; 33(2): S168-S175.

Everaerts et al., "Biomechanical properties of cabodiimide cross-linked collagen: Influence of the formation of ester crosslinks," *Journal of Biomedical Materials Research*, 2007; (85A): 547-555.

Hafemann et al. "Cross-linking by 1-ethyl-3-(3-dimethylaminopropyl)-cabodiimide (EDC) of a collagen/elastin membrane meant to be used as a dermal substitute: effects on physical, biochemical and biological features in vitro," *Journal of Material Science: Materials in Medicine*, 2001; 12: 437-446.

Zhang et al. "Microwave-assisted synthesis of Pt/CNT nanocomposite electrocatalysts for PEM fuel cells," *Nanoscale*, 2010; 2: 282-286.

Zhang et al., "Facile preparation and characterization of highly antimicrobial colloid Ag or Au nanoparticles," *Journal of Colloid and Interface Science*, 2008; 325: 371-376.

* cited by examiner

\* significantly different from 1X
^ significantly different from 2X
(p<0.05)

CONJUGATED POLYMERIC MATERIAL AND USES THEREOF

CROSS REFERENCE TO RELATED APPLICATIONS

This application claims the benefit of U.S. Provisional Application No. 61/397,100, filed Jun. 7, 2010. The contents of the aforementioned application is incorporated by reference.

GRANT CLAUSE

None.

BACKGROUND OF THE INVENTION

A. Field of the Invention

The present invention relates to collagen covalently bound to particles, which results in a material that is more resistant to degradation such as collagenase degradation. This material can be used in a wide range of applications.

B. Description of Related Art

The use of collagen in treating urinary incontinence, post heart-attack congestive heart failure, joint fractures, and congenital and age-related facial skin defects is limited by the stability and integrity of the currently available collagen materials. For example, collagen-based dermal fillers that are used to treat facial ageing (e.g., improving facial contours, ameliorating wrinkles, correction of scar depression, etc.) and to augment lips are highly susceptible to breaking down over a period of 12 months.

One proposed solution to the collagen breakdown issue is crosslinking collagen by the formation of covalent bonds between macromolecule collagen fibrils. However, the toxicity of the chemicals utilized to crosslink collagen can be a concern. For example, glutaraldehyde and hexamethylene diisocyanate become incorporated within the collagen scaffold during crosslinking and can release toxic residues into the body as the collagen is degraded. Another problem is that too much cross-linking can create a stiff and unusable collagen material.

SUMMARY OF THE INVENTION

The inventors have discovered a solution to the performance issues limiting current collagen-based products. This solution includes the use of particles having an average particle diameter of 20 to 1000 nanometers that are capable of forming covalent bonds with collagen. The conjugated material (e.g., compositions comprising the material, conjugated collagen/particles, or conjugated collagen fibril/particles) is more resistant to degradation (e.g., by collagenase), biocompatible, and results in a collagen matrix or scaffold that has an acceptable level of porosity, thereby allowing for cellular in-growth. The cellular in-growth is accelerated by the conjugated particles in the novel material. In certain instances, the conjugated material also has anti-microbial properties, which can be used to fight infection after being administered to a patient.

In one instance, there is disclosed a material comprising collagen covalently bound to particles, wherein the particles have an average particle diameter ranging from 20 to 1000 nanometers. In particular embodiments, the average particle diameter is between 50 to 1000 nanometers, although other diameter sizes and ranges are contemplated as discussed below in this paragraph. The covalent bond can be formed between reactive groups on the collagen (e.g., carboxylic acid and/or amine groups) and reactive groups on the particles (e.g., amine-reactive groups, carboxylate-reactive groups, thiol-reactive groups, and/or hydroxyl-reactive groups). For example, and in one aspect, the covalent bonds can be formed between free-carboxylic acid groups present on the collagen and amine reactive groups on the particles, wherein amide bonds can be formed between the carboxylic acid groups of the collagen and the amine-reactive groups of the particles. As explained below, particles can be functionalized to include reactive groups that are capable of reacting with carboxylic acid or amine groups of the collagen. In certain instances, the collagen can also be cross-linked either by a cross linking agent such as a carbodiimide (e.g., 1-ethyl-3-(3-dimethylaminopropyl)carbodiimide) and/or by the particles themselves (e.g., collagen can be cross-linked with the particles, wherein at least one of the particles includes at least two reactive groups, and wherein at least two covalent bonds can be formed between, for example, carboxylic acid groups of the collagen and the at least two reactive groups, wherein the two reactive groups can be formed between, for example, amine groups.). In certain aspects, the cross-linked collagen is porous and can have an average pore size ranging from 500 nanometers to 200 micrometers (and any integer or range therein such as 550, 600, 650, 700, 750, 800, 850, 900, 1000, 1100, 1200, 1300, 1400, 1500, 1600, 1700, 1800, 1900 nanometers). In particular aspects, a pore size range between 1 micrometer to 100 micrometers can be used (or any integer or range therein such as 10, 20, 30, 40, 50, 60, 70, 80, or 90 micrometers). In certain instances, the particles have an average particle diameter of 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, or 1000 nanometers. In particular embodiments, the average particle diameter ranges from 60 to 900, 70 to 800, 80 to 700, 90 to 600, 100 to 500, 150 to 400, or 200 to 300 nanometers. In certain aspects, the average particle diameter ranges from 50 to 150, 60 to 140, 70 to 130, 80 to 120, or 90 to 110 nanometers. The particles can be made up of or comprise metallic material. The metallic material can be gold, silver, platinum, titanium, nickel, or copper or any combination thereof. In particular aspects, the metallic material is gold or silver. The particles can also be made of or comprise ceramic material or biodegradable material. In certain embodiments, the ratio of particles to collagen can be a range of $1 \times 10^9$ particles per mg of collagen to $2 \times 10^{10}$ particles per mg of collagen, however broader ranges are contemplated (e.g., $1 \times 10^4$ to $1 \times 10^{14}$ per mg of collagen, and any range and integer therein). In some aspects, 2 to 4 mg of a carbodiimide cross-linking agent (e.g., EDC) per 30 mg of collagen can be used to form the covalent bonds (in particular aspects, the ratio can be 3.2 mg+/−0.8 mg of a carbodiimide cross-linking agent such as EDC per 30 mg of collagen can be used). Also, 0.5 to 0.2 mg of a carbodiimide cross-linking agent (e.g., EDC) per $1 \times 10^9$-$2 \times 10^{10}$ particles can be used to form the covalent bonds. In certain aspects, the material of the present invention can further include cells that can be used to aid in treatment options. Non-limiting examples of such cells include: embryonic stem cells, adult stem cells, induced pluripotent stem cells, and cells derived there from, cells of endodermal, mesodermal or ectodermal orgin including but not limited to epithelial cells, exocrine and endocrine cells, myoblasts, fibroblasts, osteoblasts, chondroblasts, stromal cells, hepatocytes, islet cells, neurobalsts keratinocytes, osteoclasts, osteocytes, cardiac cells, chondrocytes, endothelial cells, and/or muscle cells, and combinations thereof. The collagen that can be used includes type I, II, III, IV or V collagen, or a combination thereof. In particular embodiments, the material can be in a gel-state, a solution, a paste, electrospun micron or nano collagen, sheets of collagen, or a dehydrated rigid structure. The material can be comprised in a syringe or in an injectable solution. The material can be dermatologically acceptable composition or a dermal or epidermal skin-equivalent. In certain aspects, the amount of free carboxylic acid groups or free amine groups that are present on the conjugated collagen/particle material is at least 5, 10, 15, 20, 25, 30, 35, 40, 45, 50, 60, 70, 80, or 90% less when compared with collagen that has not been conjugated with a particle. Stated another way, at least 5, 10, 15, 20, 25, 30, 35, 40, 45, 50, 60, 70, 80, or 90% or more of the free carboxylic acid or free amine groups of the collagen are conjugated.

Also contemplated is a collagen fibril covalently bound to at least one particle, wherein the at least one particle has an average particle diameter ranging from 20 to 1000 nanometers or 50 to 1000 nanometers. In particular aspects, the covalent bond can be formed between a free carboxylic acid and/or amine group on the collagen fibril and a reactive group present on the surface of the particle. The reactive group can be, for example, an amine-reactive group, a carboxylate-reactive group, a thiol-reactive group, and/or a hydroxyl-reactive group. In one aspect, the covalent bond can be formed between free-carboxylic acid groups present on the collagen fibril and amine reactive groups on the particles, wherein amide bonds can be formed between the carboxylic acid groups of the collagen fibril and the amine-reactive groups of the particles.

In yet another embodiment, there is disclosed a method for filling voids, defects, or increasing tissue volume in a mammal, comprising administering to a patient or mammal in need thereof (e.g., human, horse, cow, pig, dog, cat, rabbit, rat, mouse, etc.) any one of the materials disclosed through this specification. The materials, conjugated collagen/particles, or conjugated collagen fibril/particles can be administered by intradermal or subcutaneous injection. The void can be a fine line or wrinkle and the appearance of the fine line or wrinkle can be reduced after administration. The materials, conjugated collagen/particles, or conjugated collagen fibril/particles can be administered to a lip of the mammal, wherein the tissue volume of the lip is increased after administration.

In a further embodiment, there is disclosed a method of augmenting soft tissue or hard tissue in a mammal in need thereof comprising administering or applying any one of the materials disclosed through this specification to the soft or hard tissue. The soft tissue can be cardiac muscle, smooth muscle, skeletal muscle, menisci tissue, cartilage, tendons, ligaments, fascia, skin, blood vessels, fibrous tissue, or extracellular matrix. For instance, the materials can be used to support myocardial muscle to a patient that is susceptible or that already has had a heart attack. With respect to hard tissue, non-limiting examples include bones or teeth. The materials can be used to treat bone fractures or can be used to enhance boney in-growth by applying the materials to bone fractures or to bones where an increase in boney in-growth is desired.

In a particular embedment there is disclosed a method for bulking articular cartilage by increasing tissue volume in a person, comprising administering to a person in need thereof any one of the materials or compositions described throughout the specification into a joint capsule.

In one aspect, there is disclosed a method of reducing collagen degradation in vitro or in vivo by enzymatic breakdown comprising conjugating collagen with particles having an average particle diameter ranging from 20 to 1000 nanometers or 50 to 1000 nanometers, wherein covalent bonds are formed between the collagen and particles, and wherein degradation of the collagen by collagenase is thereby reduced when compared with collagen that is not conjugated with particles. The conjugation can be through a covalent bond between free carboxylic acid groups or free amine groups of collagen and reactive groups present on the surface of the particles. The reactive groups can be, for example, amine-reactive groups, carboxylate-reactive groups, thiol-reactive groups, and/or hydroxyl-reactive groups. In one aspect, the covalent bond can be formed between free-carboxylic acid groups present on the collagen and amine reactive groups on the particles, wherein amide bonds can be formed between the carboxylic acid groups of the collagen and the amine-reactive groups of the particles. The method can further include administering the conjugated collagen to a mammal (e.g., intradermal or subcutaneous injection or topical application).

In yet another embodiment, there is disclosed a method of increasing cell attachment in vitro or in vivo comprising conjugating collagen with particles having an average particle diameter ranging from 20 to 1000 nanometers or 50 to 1000 nanometers, wherein covalent bonds are formed between the collagen and particles, and wherein the surface area to volume ratio of the nanoparticles attract cell re-population and collagen synthesis. The conjugation can be through a covalent bond between free carboxylic acid groups or free amine groups of collagen and reactive groups present on the surface of the particles. The reactive groups can be, for example, amine-reactive groups, carboxylate-reactive groups, thiol-reactive groups, and/or hydroxyl-reactive groups. In one aspect, the covalent bond can be formed between free-carboxylic acid groups present on the collagen and amine reactive groups on the particles, wherein amide bonds can be formed between the carboxylic acid groups of the collagen and the amine-reactive groups of the particles. The method can further include administering the conjugated collagen to a mammal (e.g., intradermal or subcutaneous injection or topical application).

In still a further embodiment, there is disclosed a method for generating tissue comprising seeding any one of the materials disclosed through this specification with embryonic stem cells, adult stem cells, induced pluripotent stem cells, and cells derived there from or seeding with cells of endodermal, mesodermal or ectodermal orgin including but not limited to epithelial cells, exocrine and endocrine cells, myoblasts, fibroblasts, osteoblasts, chondroblasts, stromal cells, hepatocytes, islet cells, neurobalsts keratinocytes, osteoclasts, osteocytes, cardiac cells, chondrocytes, endothelial cells, and/or muscle cells. The method can further include administering the conjugated collagen to a mammal.

The materials disclosed throughout the specification can also be used to treat urinary diseases (e.g., urinary incontinence) by administering to a mammal in need thereof said materials, conjugated collagen/particles, or conjugated collagen fibril/particles. By way of example, the materials can be formed into a pelvic sling or can be used with an existing pelvic sling. Alternatively, the materials can be in an injectable form and can be used as a bulking agent to reduce or prevent urinary incontinence by injecting said material into the mammal.

Also disclosed is a method for clotting blood comprising administering to a mammal in need thereof the materials disclosed throughout the specification to a site where blood clotting is desired (e.g. internal or external wounds). Non-limiting examples of external wounds include bed sores, cuts, scrapes, incisions, open wounds, loss of limbs etc.

In one particular embodiment, there is disclosed a method for treating osteoarthritis comprising administering to a mammal in need thereof any one of the materials disclosed throughout the specification. For instance, the materials can be administered to a joint capsule or cartilage as a bulking agent to promote re-growth and decrease pain.

In still another particular embodiment, there is disclosed a method for enhancing nerve growth comprising administering to a mammal in need thereof any one of the materials disclosed throughout the specification. For instance, the materials can be administered to nerves as conduits for nerve growth or re-growth.

Also disclosed is a method for making collagen/particle conjugated material of the present invention. Such a process includes 1) functionalizing the preselected particles and 2) crosslinking the functionalized particles with the soluble collagen fibers in the presence bioconjugate reagent. The process can further include an incubation period for polymerization following the crosslinking step. In one aspect, the process includes: (1) obtaining functionalized particles (e.g. metal particles such as gold functionalized with cysteamine); (2) add functionalized particles to a solution comprising EDC and NHS and optionally buffer; and (3) add collagen to the solution with mixing. In certain embodiments, the ratio of particles to collagen can be a range of $1 \times 10^9$ particles per mg of collagen to $2 \times 10^{10}$ particles per mg of collagen, however broader ranges are contemplated (e.g., $1 \times 10^4$ to $1 \times 10^{14}$ per mg of collagen, and any range and integer therein). Also, 2 to 4 mg of a carbodiimide cross-linking agent (e.g., EDC) per 30 mg of collagen can be used to form the covalent bonds (in particular aspects, the ratio can be 3.2 mg+/−0.8 mg of a carbodiimide cross-linking agent such as EDC per 30 mg of collagen can be used), and/or 0.5 to 0.2 mg of a carbodiimide cross-linking agent (e.g., EDC) per $1 \times 10^9$-$2 \times 10^{10}$ particles can be used to form the covalent bonds.

In another embodiment, there is disclosed a method for increasing cellularity, promoting an influx of cells, promoting cell adhesion, or promoting cell migration into a collagen implant or a collagen-based bulking agent, comprising using anyone of the materials or compositions disclosed throughout this specification to make a collagen implant or the collagen-based bulking agent. Also disclosed is a method for increasing cellularity, an influx of cells, promoting cell adhesion, or promoting cell migration into a collagen implant or a collagen-based bulking agent, comprising covalently binding collagen to particles to form the collagen implant or the collagen-based bulking agent, wherein covalent amide bonds are formed between free carboxylic acid groups of the collagen and amine reactive groups of the particles, and wherein the particles have an average particle diameter size ranging from 50 to 1000 nanometers. Such methods can further include administering the collagen implant or collagen-based bulking agent to a person in need thereof.

It is contemplated that the materials disclosed throughout the specification can be comprised within a dermatologically acceptable vehicle, a pharmaceutically-acceptable vehicle, or pharmacologically acceptable vehicle. Such vehicles are ones that do not produce prohibitive toxicity, incompatibility, instability, allergic response, and/or the like, when administered to a mammal such as a human. Further, such compositions can be in powdered form, dehydrated, electrospun, liquid form, gel-form, a semi-solid, or solid. In this regard, compositions of the present invention can have a viscosity range between 10 up to 100,000,000 cps, as measured on a Brookfield Viscometer using a TC spindle at 2.5 rpm at 25° C. In particular aspects, a range of 150,000 to 250,000 can be used.

Routes of administering the materials and compositions of the present invention can vary with the location and nature of the condition to be treated. By way of example, topical application, intradermal, parenteral, intramuscular, subcutaneous, percutaneous, intratracheal, intraperitoneal, direct injection (e.g., an injectable solution), and surgical (e.g., through incision and placing in target area).

It is contemplated that any embodiment discussed in this specification can be implemented with respect to any method or composition of the invention, and vice versa. Furthermore, compositions of the invention can be used to achieve methods of the invention.

"Injectable collagen" includes collagen pastes, gels, solutions, or suspensions, homogeneous or heterogeneous, which are contained in syringes, tubes or other containers equipped with appropriate plungers or systems, designed to extrude the collagen through a needle or a nozzle. Injectable collagen is designed for injection, surgical application through a trocar, or direct application on a wound surface.

"Mammals" includes humans, horse, cow, pig, dog, cat, rabbit, rat, mouse, etc.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

DESCRIPTION OF ILLUSTRATIVE EMBODIMENTS

Figure 1:
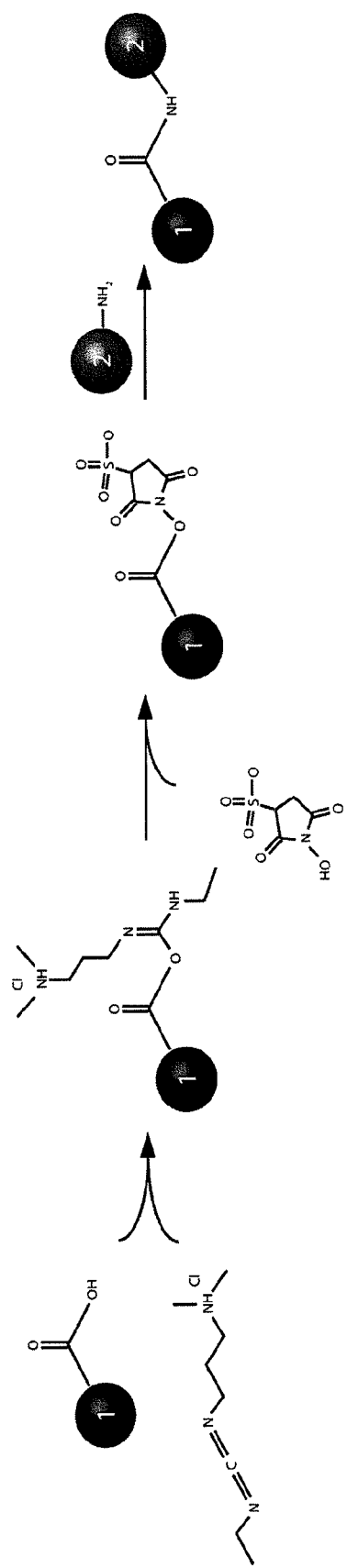
FIG. 1. A schematic diagram for covalently conjugating collagen (designated "1") with a gold particle (designated "2") via the formation of an amide bond between a free carboxylic acid group of the collagen and a reactive amine group of the functionalized particle with mercaptoethylamine (MEA). 1-Ethyl-3-[3-dimethylaminopropyl]carbodiimide hydrochloride (EDC) and N-hydroxysulfosuccinimide (Sulfo-NHS) are used to facilitate conjugation.

The inventors have discovered that by covalently binding particles to collagen at free carboxylic acid groups of collagen or collagen fibrils, degradation of collagen can be reduced. This results in a collagen-based material that is more stable when administered to a mammal to treat or prevent a particular disease or skin condition. Further, by using particles having an average particle diameter of 20 to 1000 nanometers, 50 to 1000 nanometers, or even 50 to 150 nanometers, the resulting collagen/particle material creates an environment which promotes cellular growth and infiltration (e.g., cells that are either present within the patient or cells that are incorporated into the material are attracted to the particles, which allows for a more sustained and vibrant growth of the cells than was to be expected when compared with collagen that does not include such particles) while exhibiting reduced toxicity when compared with particles that are less than 20 nanometers or less than 50 nanometers. That is to say, the inventors have discovered an effective way to stabilize collagen by reducing collagen degradation while also promoting cellular growth without the risk of toxic side effects that are currently seen in existing collagen-based materials.

Without wishing to be bound by theory, it is believed that covalent bonds formed on the free carboxylic sites of collagen hindered and/or block some of the collagenase binding sites, while the particle size provides a sufficient surface area and surface energy which allows for cellular adherence, increased cellularity, and protein adsorption, thereby promoting cellular proliferation and growth. Additionally, metallic particles may provide anti-oxidative effects which reduces reactive oxygen species and other free radicals that can damage cells, and metallic particles may provide anti-microbial effects. Further, the particle size is sufficient to reduce toxicity in the surrounding environment by preventing or reducing cellular uptake of the particles.

These and other aspects of the present invention are described in further non-limiting detail below.

A. Collagen

Collagen is a type of protein found in mammals that connects and supports bodily tissues, such as skin, bone, tendons, muscles, and cartilage. It also provides support for internal organs and is present in teeth. There are more than 25 types of collagens that naturally occur in the body, all of which can be used in the context of the present invention. The more prevalent collagens include Types I (found in skin, tendon, vascular, ligature, organs, bone), II (found in cartilage), III (found in reticular fibers), IV (forms bases of cell basement membrane) and V (found in cell surfaces, hair, and placenta). Some of the more prevalent structural features of collagen include an abundance of glycine, proline, hydroxyproline, free carboxylic acid groups, and free amine groups See Collagen Structure and Mechanics (2008).

With respect to skin, collagen provides the skin with strength, flexibility, and resilience. It also provides a framework for the growth of cells and blood vessels in skin. Collagen degradation (e.g., in aged skin, diseased, damaged skin such as scars, sun damage, acne, etc.) leads to the presence of fine lines, wrinkles, pits, nodules, creases, and the like in skin. One way to reduce the appearance of these skin defects is to inject collagen into skin, which results in filling-in the skin defects, hence a "dermal filler." Collagen also has several medical uses ranging from increasing joint mobility, treating burns and other open skin wounds, treating osteogenesis imperfect (i.e., brittle bone disease), and other medical uses disclosed and claimed throughout this specification.

Collagen that can be used in the context of the present invention can be extracted from a wide range of sources (e.g., porcine, bovine, human, fish, rat tail, etc.). Non-limiting collagen materials that can be used include recombinant human collagen, tissue engineered human-based collagen, porcine collagen, human placental collagen, bovine collagen, autologous collagen, collagen fibers, and human tissue collagen matrix. Further collagen and collagen-based products that can also be used are commercially available, non-limiting example of which are listed in International Cosmetic Ingredient Dictionary and Handbook, 12$^{th}$ edition, volume 1, page 656 (2008), which is incorporated by reference. Additional non-limiting examples of commercially available collagen products that can be used in the context of the present invention include Cosmoderm® 1 and 2, CosmoPlast®, Zyderm®, and Zyplast®, all of which are manufactured by Inamed Corp., Santa Barbara Calif. Evolence®. In particular embodiments, porcine collagen is used.

B. Particles and Covalent Bond Formation with Collagen

As explained above, particles having an average particle diameter size of 20 to 1000 nanometers, 50 to 1000 nanometers, or 50 to 150 nanometers can be used in the context of the present invention. The average particle diameter size can be determined by Dynamic Light Scattering (DLS). DLS is a technique that provides the size distribution profile of particles in suspension. The average particle size can be determined from the size distribution profile (Thomas (1987)) In addition, there are several resources available by which one can purchase or obtain particles having a particular diameter size (e.g., PELCO® NanoXact & BioPure Gold and Silver Colloids from Ted Pella, Inc. (Redding, Calif.); Accurate Spherical Gold Nanoparticles, Gold Nanorodz, Microgold, Gold Nanobeads, Gold Nanowires, Platinum, Palladium, and Trimetallic Nanoparticles from NanoPartz, Inc. (Loveland, Colo.); and Gold Nanoparticles, Silver Nanoparticles, Platinum Nanoparticles, Palladium Nanoparticles, and Green Nanoparticles from Nanoparticle Biochem Inc, (Columbia, Mo.)).

The particles that can be used can include or be made up of either metallic material, ceramic material, and/or biodegradable material or a combination thereof. With respect to metallic particles, non-limiting examples include gold, silver, platinum, titanium, nickel, and/or copper. In particular instances, the material used for the particles (e.g., gold or silver) can have antimicrobial properties, which can be useful to reduce the likelihood of infection. Further, such particulate material can function as an electron acceptor and can therefore reduce free-radical damage caused by reactive oxygen species ("ROS").

The particles that are used in the context of the present invention can include reactive groups, non-limiting examples of which include amine-reactive groups, carboxylate-reactive groups, thiol-reactive groups, carboxylic acid reactive groups, or hydroxyl-reactive groups, or any combination thereof. Such functionalized particles are commercially available and can be made by a person having ordinary skill in the art. Further, the use of cross-linking agents can be used to promote formation of covalent bonds between collagen and the particles and can also be used to promote cross linking between the collagen itself (e.g., cross-linking of the collagen can occur via the particles when the particles have at least two functional groups present where one of the functional groups forms a covalent bond with collagen and the other function group forms a second covalent bond with collagen or in instances with the cross-linking agent forms covalent bonds between the collagen itself). A non-limiting process is provided below.

In particular embodiments, the particles include amine reactive groups that are capable of forming an amide bond with free carboxylic acid groups present in the collagen. By way of example, FIG. 1 describes such an embodiment. In particular, FIG. 1 illustrates that the carboxylic acid functional group on collagen fiber 1, is first activated by EDC, then though nucleophilic addition to generate amide bond between collagen fiber and the metallic nanomaterial 2. EDC forms an active ester functional group with carboxylate groups on the collagen fibrils; but hydrolysis occurs rapidly and thus EDC is typically coupled with sulfo-NHS to form a sulfo-NHS ester intermediate. The ester intermediates then react with amine groups on the metallic nanoparticles. The EDC-sulfo-NHS facilitates an amide bond between the collagen and MEA attached to the particle with release of an isourea by-product. NHS is commonly added to the EDC to enhance stability and binding.

The toxicity of the chemicals utilized to promote formation of covalent bonds between collagen and the particles and to crosslink collagen should be considered. Glutaraldehyde, hexa-methylene diisocyanate, and EDC are all commonly used crosslinkers, but only the carbodiimide is non-toxic and does not become incorporated within the collagen scaffold during crosslinking (see Shanmugam (2006), Lee (2001), Rault (1996), Grtzer (2001), Chan (2005), Billiar (2001), Pieper (1999), Haidekker (2006)). Conversely, glutaraldehyde and hexamethylene diisocyanate do become incorporated within the scaffold and may release toxic residues into the body as the scaffold is degraded. Additionally, excessive crosslinking may drastically change the microstructure and render the scaffold so resistant to degradation that it becomes encapsulated by a fibrous layer and is never replaced by healthy tissue.

C. Process for Making Conjugates

The following procedure is a non-limiting way to make the conjugated materials of the present invention:

(1) Obtain non-polymerized collagen:
  a. Mix 30 mg of lyophilized collagen with 1 mL of acetic acid (10 mM).
  b. Dissolve for 3 hours at room temperature by turning the vial slowly.

(2) Prepare concentrated functionalized Nanomaterials:
  a. Spin 1.344 mL of 100 nm gold nano-particles suspension (AuNP concentration $5.6 \times 10^9$ particles/mL for 5 min at 7,000 rpm.
  b. Remove 1.144 mL of water leaving 0.2 mL of AuNP in water suspension.
  c. Add 9.1 uL of 0.12M cysteamine (=beta-mercaptoethylamine; MEA) to 0.2 mL of AuNP suspension.
  d. Mix to yield functionalized nanomaterials by pipette, turning over 3 times, or by vortex for 5 seconds in room temperature.

(3) Prepare 10× phosphate buffer saline (PBS) solution (4) Dissolve 0.0032 g of EDC (1-ethyl-3-[3-dimethylaminopropyl]carbodiimide hydrochloride) and 0.00424 g sulfo-NHS (N-hydroxysuccinimide) in 0.2 mL of 10×PBS buffer.

(5) Add all 0.209 mL of functionalized nanomaterials to 0.2 mL of EDC and NHS in 10×PBS buffer if rat collagen is used. If human collagen is used then the same buffer system can be used or a different one can be used (e.g., sodium phosphate dibasic buffer system.

(6) Add 0.045 mL of 1M NaOH to nanomaterials in PBS buffer.

(7) Mix 0.454 mL of functionalized nanomaterials EDC, NHS in 10×PBS buffer with NaOH to 1 mL of collagen solution at 30 g/L.

(8) Pipette up and down 5-10 times to ensure mixture.

(9) Place in incubator at 37° C. for 90 minutes to polymerize.

(10) Remove the newly formed scaffold from the incubator and condition to be injected out of 30 Ga needle or prepare scaffold in other forms.

As noted above, this process is a non-limiting example of one way to make a particle/collagen conjugate within the context of the present invention. Modifications and variations are contemplated and can be made to prepare a desired end-product for a particular treatment option.

D. Compositions of the Present Invention

As noted above, the conjugated materials of the present invention (e.g., conjugated collagen/particles, or conjugated collagen fibril/particles) can be included in compositions such as injectable compositions, topical compositions, implantable compositions, and can take a variety of forms (e.g., liquid, powdered, dehydrated, semi-solid, gel, solid, rigid, etc.). The compositions can also include additional ingredients such as cosmetic ingredients (both active and non-active) and pharmaceutical ingredients (both active and non-active) depending on the nature of the route of administration and/or the particular disease to be treated.

The CTFA International Cosmetic Ingredient Dictionary and Handbook (2008), 12$^{th}$ Edition, describes a wide variety of non-limiting cosmetic ingredients that can be used in the context of the present invention. Examples of these ingredient, which can be useful for topical products include adsorbents, emulsifiers, stabilizers, lubricants, solvents, moisturizers (including, e.g., emollients, humectants, film formers, occlusive agents, and agents that affect the natural moisturization mechanisms of the skin), water-repellants, vitamins (e.g., A, B, C, D, E, and K), botanical extracts, anti-microbial agents, antioxidants (e.g., BHT and tocopherol), chelating agents (e.g., disodium EDTA and tetrasodium EDTA), and preservatives.

Non-limiting examples of pharmaceutical ingredients that can also be used include analgesics, anesthetics, anti-inflammatory agents including non-steroidal anti-inflammatory drugs, antibiotics, antifungals, antivirals, antimicrobials, anti-cancer actives, antpsoriatic agents, antiseborrheic agents, biologically active proteins and peptides, burn treatment agents, cauterizing agents, skin protectant/barrier agents, steroids including hormones and corticosteroids, wound treatment agents, wound healing agents, etc.

E. Kits

Kits are also contemplated as being used in certain aspects of the present invention. For instance, a material or composition of the present invention can be included in a kit. A kit can include a container. Containers can include a bottle, a metal tube, a laminate tube, a plastic tube, a syringe, a dispenser, a pressurized container, a barrier container, a package, a compartment, or other types of containers such as injection or blow-molded plastic containers into which the materials or compositions are retained. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Functionalized AuNP

Figure 2:
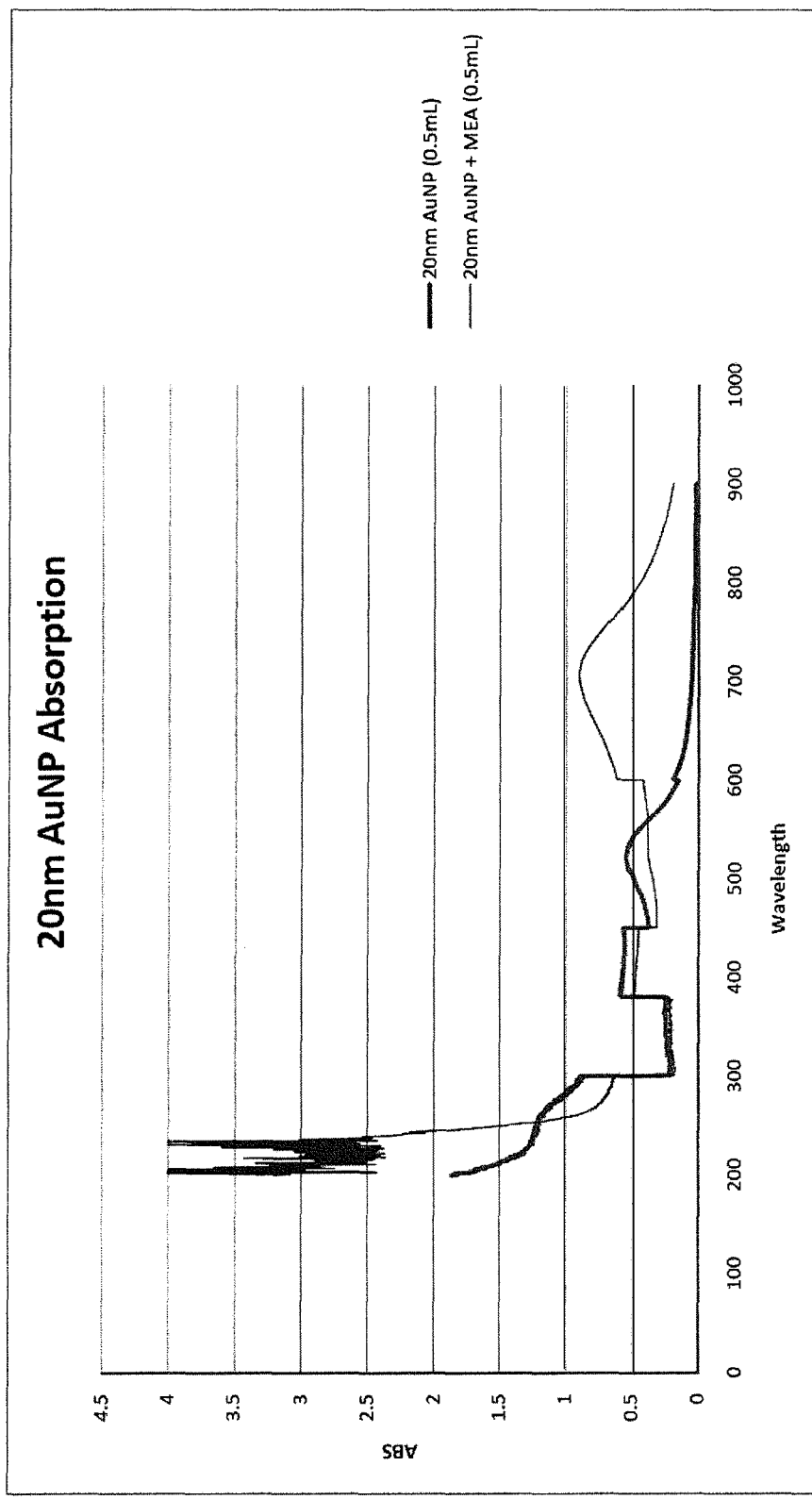
FIG. 2. UV spectrum illustrating gold particles functionalized with β-mercaptoethylamine (MEA).

Gold nanoparticles (AuNP) having an average particle diameter size of 20 nanometers were functionalized with 15 uM of 2-mercaptoethylamine (MEA). FT-IR spectrometry confirms the presence of the functionalize groups on the AuNP. Additionally, the optimal concentration of MEA is determined through the use of UV-Vis spectroscopy before and after the addition of an electrolyte (10% NaCl). The optimal concentration was defined as the concentration of MEA that stabilized the AuNPs, preventing aggregation and maintaining dispersion even after the addition of 10% NaCl. As shown in FIG. 2, the UV/Vis spectrum undergoes a shift in absorbance peak when functionalized with MEA. The functionalized nanomaterials are then mixed with 2 mM EDC (1-Ethyl-3-(3-dimethylaminopropyl)-carbodiimide) and 5 mM sulfo-NHS (sulfo-N-Hydroxysuccinimide) in order to facilitate covalent binding to the carboxyl groups on the collagen fibrils.

Example 2

AuNP-Collagen Conjugated Material

To form AuNP-collagen gel scaffolds, 2.5 mL rat tail collagen (concentration of 9 mg/ml) was added to a mixture of 0.5 mL 10×PBS, 0.057 mL 1M NaOH, 4.0 mg EDC, 5.3 mg sulfo-NHS and 0.5 mL of functionalized AuNP solution (9.408×10$^9$ particles). Next, the matrix was placed in an incubator at 37° C. for 90 minutes for polymerization and crosslinking. The ratio between the number of nanoparticles and collagen solution is 3.8×10$^9$ AuNP per 9 mg rat tail collagen.

Figure 3:
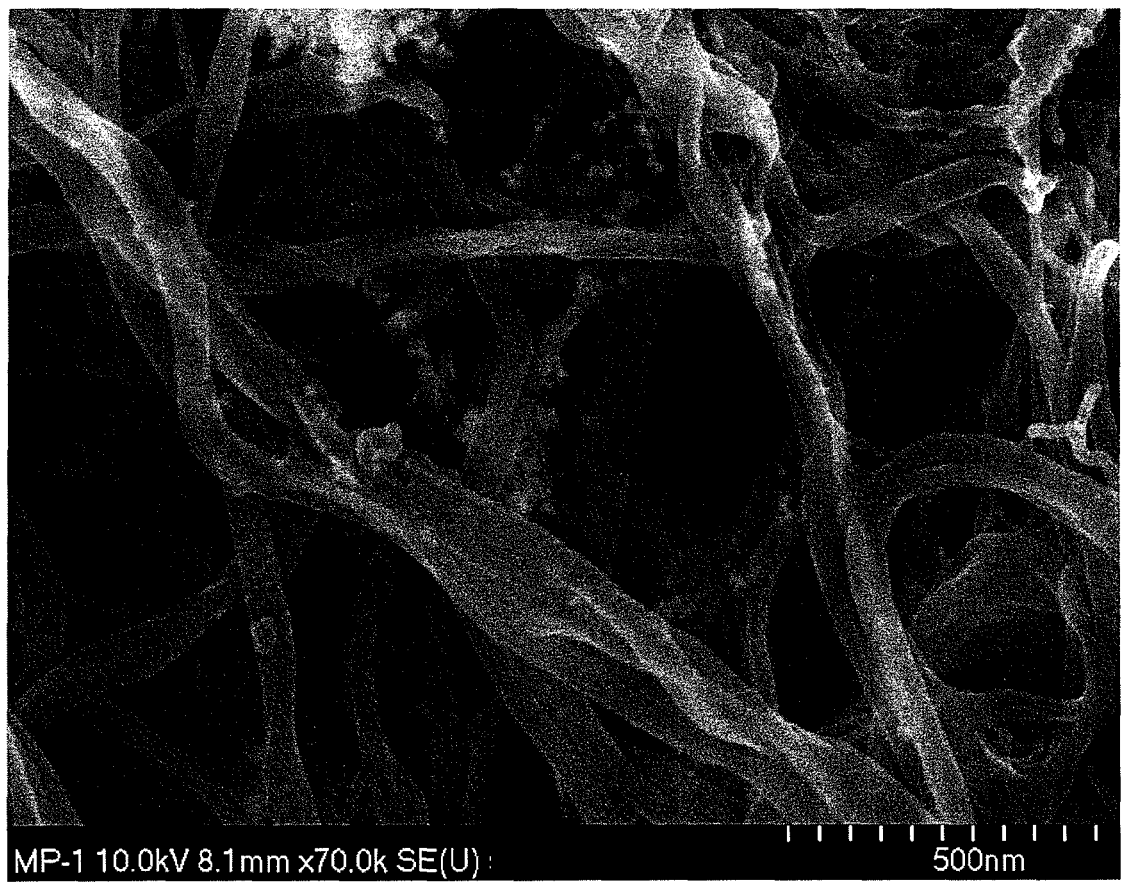
FIG. 3. SEM of a gold particle conjugated gel scaffold.

FIG. 3, which is an SEM of an exemplary collagen gel scaffold with 20 nm AuNP attached through a cysteine EDC/NHS crosslinker. SEM characterizes the distribution and density of the gold nanoparticles in the collagen gel scaffolds. As shown in FIG. 3 displaying an SEM of the AuNP-collagen material at 100×, AuNPs are present throughout the scaffold, which indicates that the AuNPs are binding to the collagen fibrils. The gels undergo extensive washing which removes any unbound AuNPs from the collagen scaffold (Haidekker (2006)).

Figure 4:
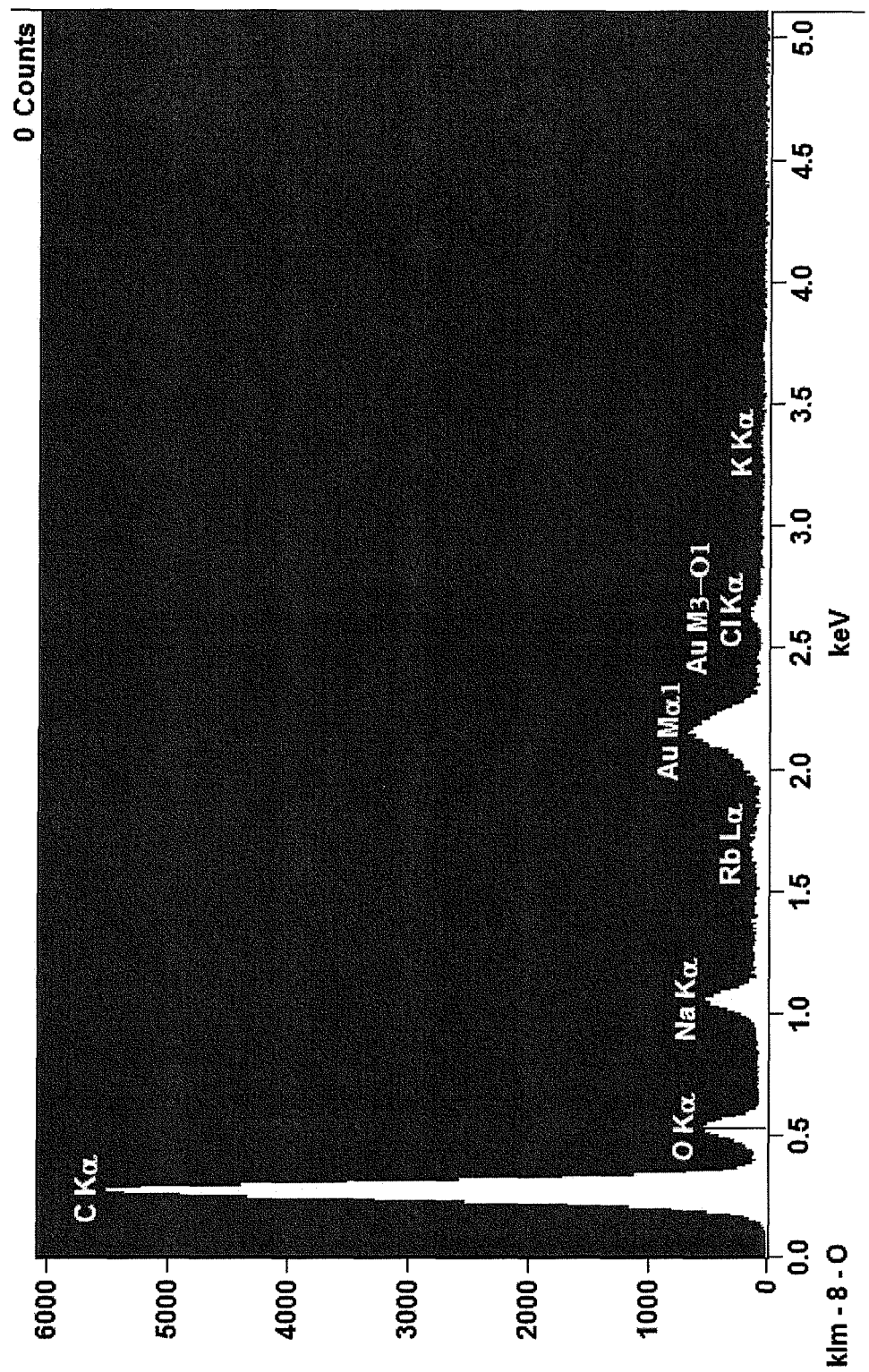
FIG. 4. EDS image demonstrating that crosslinked particles are gold particles within the scaffold structure.

While the SEM micrograph shown in FIG. 3 confirms the attachment of the nanoparticles, FIG. 4 confirms that the attached particles are gold particles. FIG. 4 is an EDS (Energy Dispersive Spectroscopy) image of the gold nanoparticles covalently immobilized to the collagen scaffold.

Example 3

Degradation Assay

Figure 5:
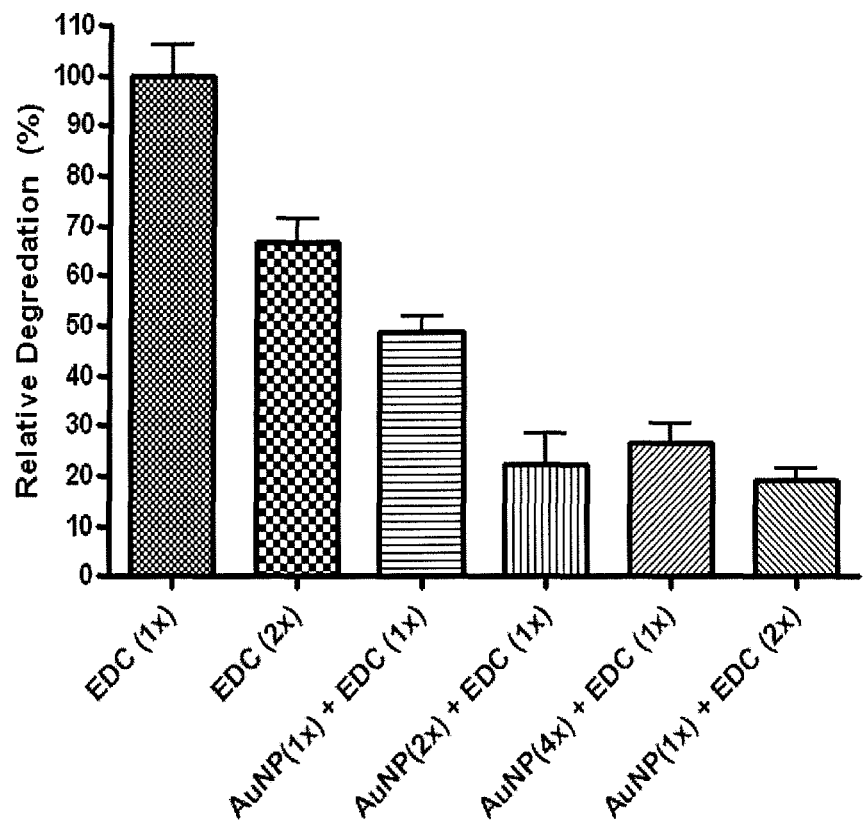
FIG. 5. Bar diagram illustrating the improved resistance to collagenase degradation of collagen conjugated with gold particles.

As noted above, the inventors believe that by blocking a portion of the carboxylic acid binding sites on collagen fibrils with particles, a decrease in collagenase activity and resulting decrease in degradation rates of collagen would occur. This has been confirmed experimentally (see data in FIG. 5). As illustrated in FIG. 5, the effects of the nanomaterials on collagen degradation at different concentrations are examined and compared with the samples without nanomaterials. The diameter size of the gold nanoparticles (AuNP) was constant for each sample at 100 nm and the process by which the conjugated material was made is that described in Section C ("Process for Making Conjugates") of the Description of Illustrative Embodiments of this specification, which is incorporated into this example by reference. The concentration varied between samples (1×, 2×, 4×). Concentration of the zero length crosslinker 1-ethyl-3-(3-dimethyl aminopropyl)carbodiimide (EDC) also varied between samples. The control sample contained rat tail collagen crosslinked by ECD (1×) without nanoparticles. A collagenase assay was performed to test the biological stability of the crosslinked samples. The biological stability through degradation of the samples was measured by the amount of hydroxyproline release. The percent of the degraded matrix is reported relative to the control (EDC 1× no nanoparticles) in FIG. 5. The error bars represent standard deviation calculated from eight samples. Simply doubling the concentration of the zero length crosslinker ECD significantly decreased the degradation of the scaffold by 30% ($p<0.001$). Adding gold nanoparticles to the matrix also had a significant effect of decreasing the degradation of the matrix ($p<0.001$). A 1× concentration of 100 nm gold nanoparticles reduced degradation of 50% while a 2× concentration was significantly reduced to as little as at 7% degradation ($p<0.01$). There are no significant differences between AuNP (2×) and AuNP (4×) as well as AuNP (1×) with an increase of EDC to 2× concentration. The results indicate that addition of 100 nm gold nanoparticles aids in the proteolytic resistance of the collagen and increase the biological stability of the matrix. The results also indicate that the attachment of the nanomaterials to the collagenase binding sites along the collagen fibrils decreases the degradation rate of the scaffold. The results further indicate that a range of sized and shaped nanomaterials, such as nanorods with diameters between about 20 to about 1000 nm can be utilized.

Moreover, through functionalizing the nanomaterials with amine groups (MEA), the number of bonds formed between the nanomaterial and collagen may be maximized. Additionally, each nanoparticle may provide multiple (more than two) sites of attachment, while most crosslinking agents typically provide a two-point link between collagen fibrils. This approach may enable fabrication of specific pre-determined collagen matrix pore sizes optimal for tissue ingrowth and native collagen deposition. Since gold nanomaterials act as free radical scavengers, the scaffold will also contribute to antioxidant effects while also provide antimicrobial effects.

Other proteins may be conjugated to the nanomaterials to facilitate specific interactions once inserted into the body. For example, fibrin may be added to the nanomaterial with MEA to assist in clotting of blood during wound healing.

Example 4

Cell Viability Assay

Figure 6:
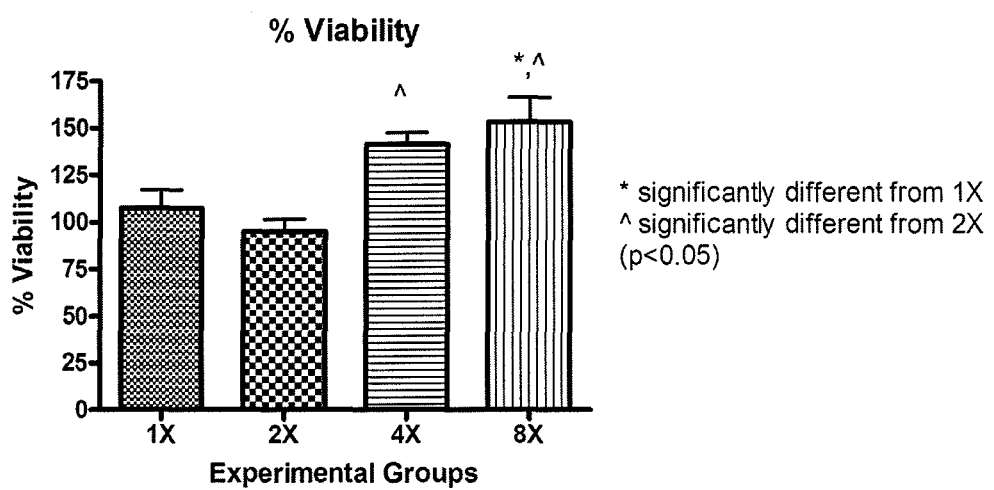
FIG. 6. Bar diagram illustrating cell viability in the presence of collagen conjugated with gold particles.

FIG. 6 provides data showing the effect of the gold nanoparticles used on cell viability via an WST-1 viability assay. Particularly, collagen scaffolds with gold nanoparticles as prepared in Example 3 in concentrations of 1×, 2×, 4×, and 8× were incubated with cells for 3 days. The viability of the cells was determined by conversion of WST-1 to an absorbance value recorded with UV-Vis. The results shown in FIG. 3 indicate viability of the control is not significantly higher than cell viability in the presence of nanoparticles. Therefore, nanomaterials have a very low cytotoxicity. With a greater absorbance reading from the higher concentration of gold nanoparticles, it is suggested that there was a larger turnover of cells in the presence of gold nanoparticles to convert more WST-1 or the number of binding sites at 2× concentration of AuNP is saturated leaving gold nanoparticles in the media and interfering with the UV-Vis absorbance values.

Example 5

Carboxylic Acid Binding Analysis

Figure 7:
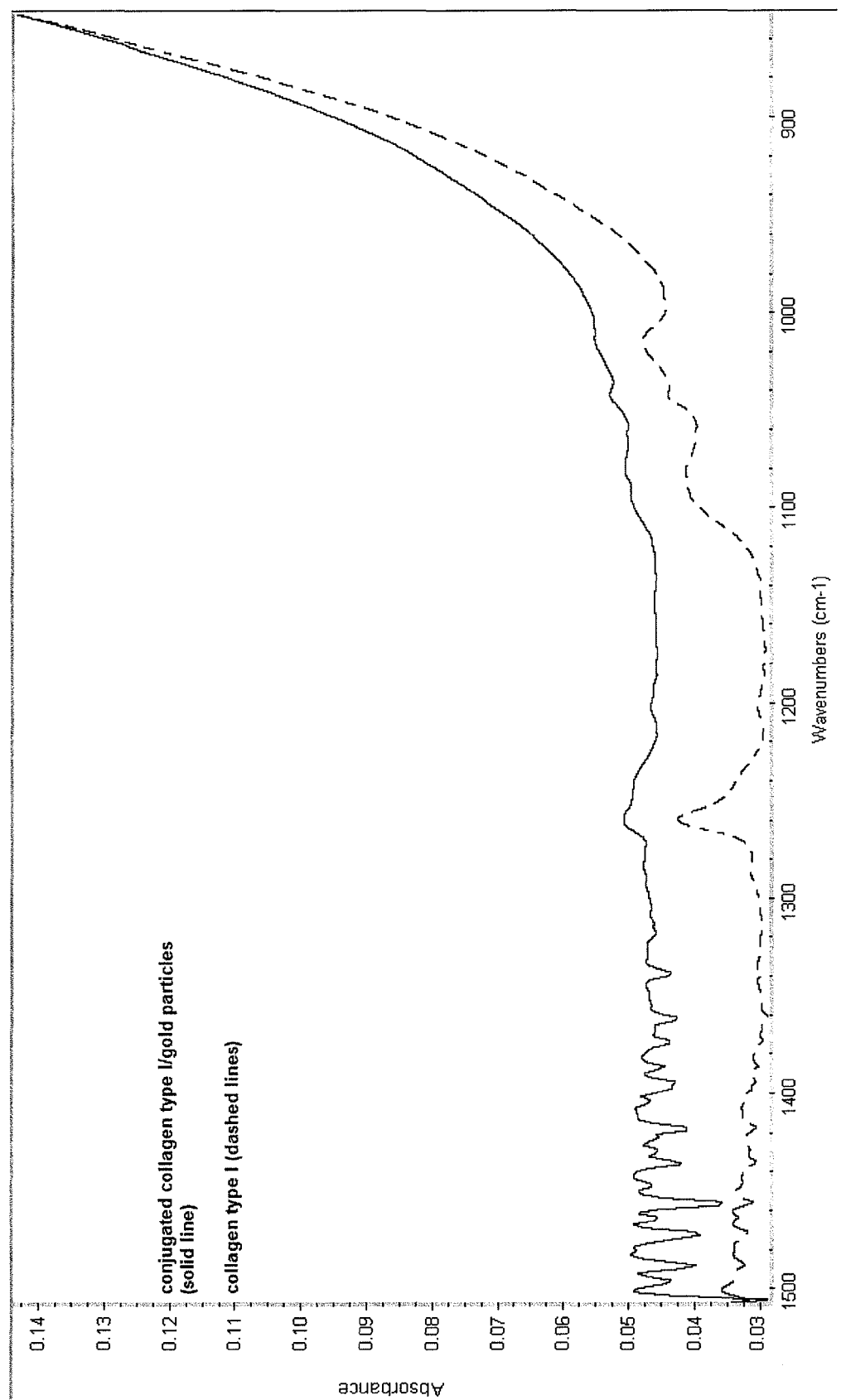
FIG. 7. Fourier Transform Infrared Spectroscopy of collagen with and without gold particles illustrating an 18% decrease in free carboxylic acid groups in conjugated collagen/gold particle material when compared with collagen alone.

The collagen scaffolds as prepared in Example 3 was analyzed to determine the amount of free carboxylic acid groups remaining on the scaffolds. In particular, Fourier Transform Infrared Spectroscopy was used on the scaffold with and without the gold particles. This technique is used to indicate a reduction in peak at the carboxylic acid sites showing the binding of the gold to the COOH on the collagen. As illustrated in FIG. 7, a decrease in peak at 1125-920 nm area was observed, which is indicative of a reduction in the C—OH bond (free COOH groups). The area under the curve went from 0.3680 to 0.3, which is an 18% decrease in free carboxylic acid groups on the collagen/particle conjugate scaffold.

Example 6

In Vitro Assessment of Cellularity, Cellular Retention, and Extracellular Matrix Production This example provides data showing the effects of conjugated collagen/particle material on the cellularity, cellular viability, extracellular matrix production, and cellular distribution when compared to untreated controls.

Materials and Methods

Scaffold group assignments: Five different combinations of gold nanoparticales and collagen gels were evaluated. The groups were numbered 1 through 5 and are outlined in Table 1. A total of 10 constructs were seeded with dermal fibroblasts and incubated for 7 and 14 days. A total of 50 samples were analyzed.

TABLE 1

| Group | Group 1: Control Collagen + EDC | Group 2: Collagen + EDC + 2× AuNP | Group 3: Collagen + EDC + 1× AuNP | Group 4: Collagen + EDC + 4× AuNP | Group 5: Collagen + ½ EDC + 2× AuNP |
|---|---|---|---|---|---|
| Day 7 | n = 5 | n = 5 | n = 5 | n = 5 | n = 5 |
| Day 14 | n = 5 | n = 5 | n = 5 | n = 5 | n = 5 |

Fibroblast harvest and culture: Skin dermis was harvested from dogs humanely euthanized by an overdose of barbiturate for reasons unrelated to this study. Tissue was placed in Dulbecco's Modified Eagle's Media with 10% fetal bovine serum, 0.008% Hepe's buffer, 0.008% non-essential amino acids, 0.002% Penicillin 100 IU/mL streptomyic 100 ug/mL, amphoterocin B 25 ug/mL, 0.002% L-ascorbate, 0.01% L-glutamine (DMEM+FBS) for transport. The dermal tissue was sectioned into 2 mm×2 mm pieces using a #10 scalpel blade under sterile technique. The tissue fragments were combined with sterile Type IA clostridial collagenase solution (Sigma, USA), at a concentration of 7.5 mg/mL of RPMI 1640 solution. The mixture was agitated in an incubator at 37° C., 5% CO2, 95% humidity for 6 hours. The digested solution was centrifuged at 1000 RPM for 10 minutes. The supernatant was decanted and the cellular pellet re-suspended in 5 mL of DMEM+FBS. The flasks were incubated at 37° C., 5% CO2, 95% humidity with sterile medium change performed every 3 days. Fibroblasts were monitored for growth using an inverted microscope until observance of 95% cellular confluence per tissue culture flask. Cells were transferred to 75 mL tissue culture flasks through subculturing until the 3rd passage is achieved and then frozen for future use. Cells were subsequently thawed, released from monolayer and put into solution prior to use.

Scaffold seeding: Collagen gels 250 µl in approximate volume were fashioned from each of group and treatments. Ten (n=10) constructs of each group were placed in individual wells of a tissue culture plate in PBS for 24 hours, placed inside sterile incubators at 37° C., 5% CO2, 95% humidity as a pre-soaking conditioning. Previous microbial culture and sensitivity examinations confirmed no growth after 3 days of culturing of the constructs for a period of 3 days. After pre-soaking, media was removed from each well and replaced with the fibroblast cell solution at a concentration of $1 \times 10^6$ cells/ml. Constructs were cultured statically with the cell solution for 24 hours, at which time the cell solution was replaced with DMEM+FBS culture media for the duration of the study.

Construct harvest and assessment: Five (n=5) constructs were harvested from each group at days 7 and 14. Cross sections were taken from each construct for cellular viability and distribution assessment. Cell viability was determined with the use of ethidium homodimer-1 (4 uL/ml PBS) and Calcein AM (acetoxymethylester) (0.4 ul/ml PBS) fluorescent stains (LIVE/DEAD Viability/cytotoxicity Kit, Molecular Probes Co.) and the use of ultraviolet microscopy. One millimeter sections were made and incubated with the staining agents for 20 minutes at room temperature, placed on a glass microscope slide, moistened with several drops of PBS, and stained using the fluorescent double labeling technique. The sections were examined under 10× magnification. Images of each section were digitally captured by an Olympus DP-70 (Olympus, Melville, N.Y.) digital camera and saved as Tiff files. The remainder of each construct was lyophilized and a dry weight obtained and then mixed with 1 ml Papin Solution. Portions of each digest were used to determine GAG content by the dimethylmethylene blue assays, and collagen content by determining hydroxyproline concentrations. The remaining solution was incubated at 60° C. in a water bath for 4 hours. The Quant-iT PicoGreen™ double stranded DNA quantification assay (Invitrogen) was used to determine the cellularity of the remaining scaffold. Double stranded DNA extracted from bovine thymus was mixed with TE buffer (Invitrogen) to create standard DNA concentrations of 1,000, 100, 10 and 1 ng/ml. The standards and 100 ul of each papain digested sample (used in the above GAG and hydroxyproline assays) were added to a 96 well plate. 100 uL of 2 ug/ml of Pico Green reagent was added to each well and the plate incubated for 5 minutes. Sample fluorescence was read at 485 nm excitation/528 nm emission by the Syngergy HT-KC-4 spectrophotometric plate reader (BioTec, Winooski Vt.). Absorbances were converted to ng/l concentrations and total double stranded DNA yield expressed in ng using FT4 software (BioTec, Winooski Vt.).

Each data set was examined and outliers were determined by those values that were more or less than 2 standard deviations outside of the remaining data set, and those values discarded. Differences within and between groups were analyzed statistically with a one-way ANOVA test with difference between individual groups determined by various post-hoc all-pairwise examinations with statistical significance set at $p<0.05$.

Results

Figure 8:
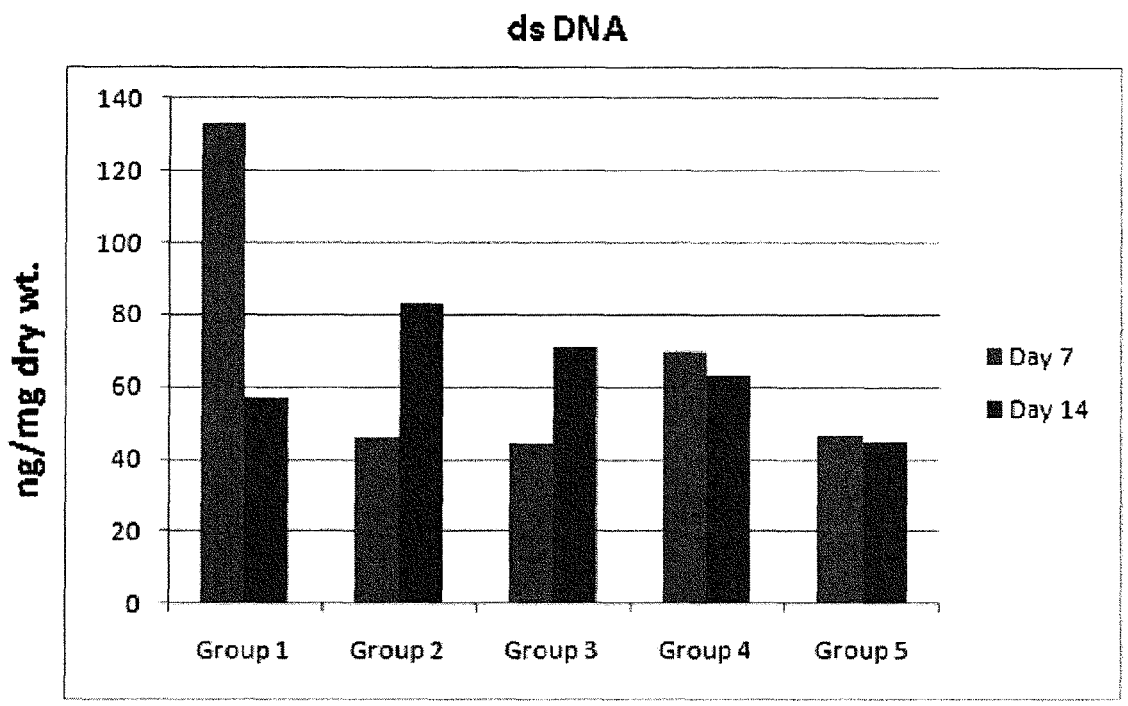
FIG. 8. DNA concentrations per scaffold group and treatment over time. Day 7 is left bar, and Day 14 is right bar for each group, respectively.

Ds DNA assessment as a measure of cellularity: As illustrated in FIG. 8, Day 7: Group 1 possessed significantly higher amounts of DNA than groups 2,3 and 5. No other significant differences were detected. Day 14: Group 2 possessed significantly higher amounts of DNA than group 5. No other significant differences were detected. Groups 1 showed a significant decline in DNA content over time, whereas Groups 2 and 3 showed an increase in DNA between the two time points. No other significant differences were detected.

Figure 9:
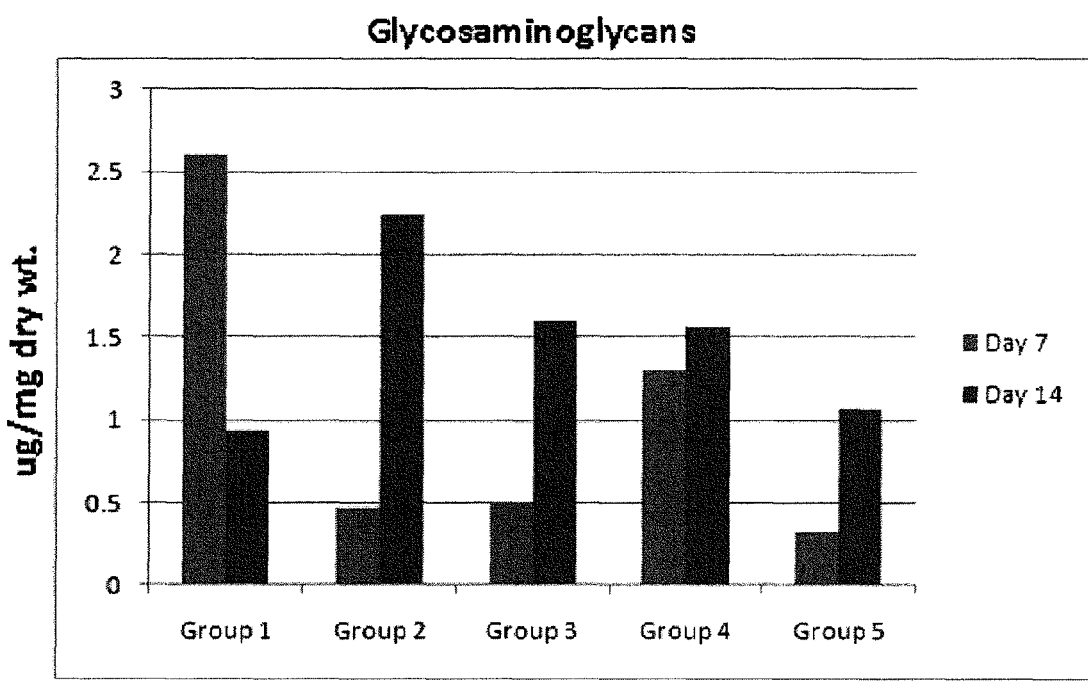
FIG. 9. Glycosaminoglycans (GAG) concentrations per scaffold group and treatment over time. Day 7 is left bar, and Day 14 is right bar for each group, respectively.
Figure 10:
FIG. 10. Live/Dead staining of all groups at Day 7 demonstrating high viability and cellularization.

Glycosaminoglycans (GAG) assessment: As illustrated in FIG. 9, Day 7: Group 1 possessed significantly higher amounts of GAG than group 5. No other significant differences were detected. Day 14: Group 2 possessed significantly higher amounts of GAG than groups 1 and 5. No other significant differences were detected. Group 1 showed a significant decline in GAG content over time, whereas Groups 2 and 3 and 5 showed an increase in GAG between the two time points. No other significant differences were detected.

Figure 11:
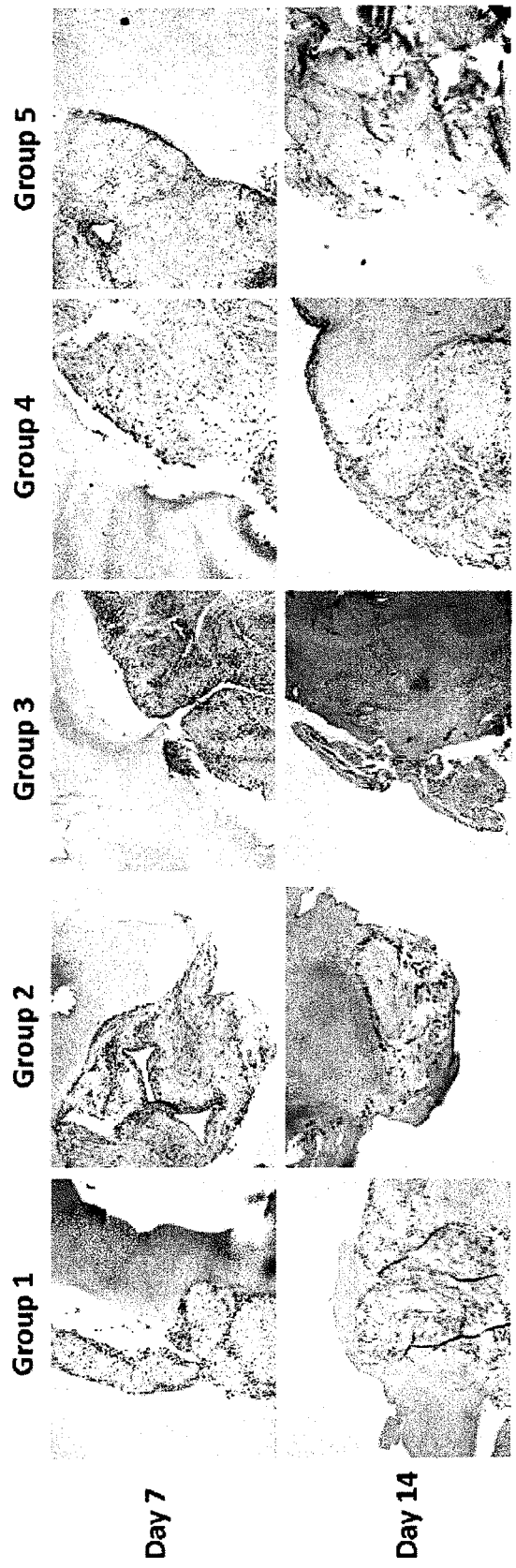
FIG. 11. Cellularization of the groups at two time points demonstrating surface proliferation at Day 7 with more elaborate interior penetration at Day 14. Cellularization of the AuNP associated channels and cavities was noted.

Cellular viability/integration assessment: Cellular viability was subjectively >95% in all groups at all time points (FIG. 11). Marked cell rafting was evident in all groups making specific viability quantification impossible via computer image analysis due to the overwhelming confluence of viable cellularity. No group demonstrated what would be interpreted as indications of cellular death. Each group demonstrated cellular adherence, retention and proliferation (FIG. 12). The day 7 groups demonstrated more evidence of cellular surface proliferation in large rafts, whereas by day 14, deeper penetration into the interior of the gel constructs was witnessed in each group. Subjectively, no difference could be detected in the degree or extent of cellular penetration between groups. In those sections where the AuNP-associated cavities in the gel were witnessed, cellular proliferation was noted to be abundant along the channels (see Day 7, Groups 2 and 5).

Conclusions

These data in Example 6 suggest that although initial cellularization of collagen gels appeared to be most optimal in the non-treated gels, longer term analysis revealed that, in general, the AuNP treated groups appeared to either retain cells or foster their proliferation better than non-treated gel constructs. It should be noted that these observations are largely based on trends only as at Day 14, the only statistical difference regarding DNA content among groups was Group 2 possessing more cellularity that Group 5. The difference in treatment between these two groups was doubling the EDC concentration in Group 5 which may impart a deleterious effect on cellular retention or proliferation. But examining the two time points within each treatment, Group 1 is the only group which demonstrated a significant decline in cellularity over time, whereas Groups 2 and 3 showed increases. Although cellular mitogenesis or proliferation was not specifically examined here, this increase in cellularity in those groups was likely a result (in part) of increasing cellularity as no additional cells were added at any time point. All groups demonstrated the ability to retain cells and foster their integration into the interior of the gel constructs over time without evidence of detectable cell death. Based on the paired dsDNA/cell viability data, it appears as though cells were less successfully retained (but did not necessarily undergo increasing amounts of cell death) in Group 1 between days 7 and 14, thus implying that the treated groups also favored cellular retention better, especially in Groups 2 and 3 (2× and 1× AuNP concentrations). This increase in cellularity was likely responsible for a corresponding large increase in GAG production in Group 2 at Day 14. With respect to the examination of hydroxyproline as a determinant of collagen production, the activity of Groups 1,2 and 3 was very similar at both time points. Interestingly, Group 4 (4× AuNP) demonstrated lower levels of HP concentrations, especially at Day 14. Group 5 showed an initial spike in HP content which declined significantly over time.

All of the materials, compositions, or methods disclosed and claimed in this specification can be made and executed without undue experimentation in light of the present disclosure. While the materials, compositions, or methods of this invention have been described in terms of particular embodiments, it will be apparent to those of skill in the art that variations may be applied to the materials, compositions, or methods without departing from the concept, spirit and scope of the invention

REFERENCES

The following references, to the extent that they provide exemplary procedural or other details supplementary to those described in this specification, are incorporated by reference.

Sangaraju Shanmugam, B. Viswanathan, T. K. Varadarajan. A novel single step chemical route for noble metal nanoparticles embedded organic-inorganic composite films. Materials Chemistry and Physics 95 (2006) 51-55.

C. R. Lee, A. J. Grodzinsky, M. Spector. The effects of crosslinking of collagen-glycosaminoglycan scaffolds on compressive stiffness, chondrocyte-mediated contraction, proliferation and biosynthesis. Biomaterials. 22: 3145-3154, 2001.

I. Rault, V. Frei, D. Herbage, N. Adbul-Marak, A. Hue. Evaluation of different chemical methods for crosslinking collagen gel, films, and sponges. J Biomed Mater Res. 7: 215-221, 1996.

P. F. Gratzer, J. M. Lee. Control of pH alters the type of crosslinking produced by 1-ethyl-3-(3-dimethylaminopropyl)-carbodiimide (EDC) treatment of acellular matrix vascular grafts. J Biomed Mater Res. 58: 172-179, 2001.

B. P. Chan, C. Amann, A. N. Yaroslaysky, C. Title, D. Smink, B. Zarins, I. E. Kochevar, R. W. Redmond. Photochemical repair of Achilles tendon rupture in a rat model. J Surg Res. 124: 274-279, 2005.

K. Billiar, J. Murray, D. Laude, G. Abraham, N. Bachrach. Effects of carbodiimide crosslinking conditions on the physical properties of laminated intestinal submucosa. J Biomed Mater Res. 56: 101-108, 2001.

J. S. Pieper, A. Oosterhof, P. J. Dijkstra, T. H. van Kuppevelt. Preparation and characterization of porous crosslinked collagenous matrices containing bioavailable chondroitin sulphate. Biomaterials. 20: 847-858, 1999.

Haidekker M A, Boettcher L W, Suter J D, Rone R, Grant S A. Influence of gold nanoparticles on collagen fibril morphology quantified using transmission electron microscopy and image analysis. BMC Med Imaging 2006; 6:4.

P. Frantzyl (Editor), Collagen: Structure and Mechanics (2008).

J. Thomas, Journal of Colloid and Interface Science, May 1987, v 117:1 p. 187-192.

The invention claimed is:

1. A composition comprising collagen covalently bound to particles, wherein covalent amide bonds are formed between free carboxylic acid groups of isolated or purified collagen and amine reactive groups of the particles, wherein the particles have an average particle diameter size ranging from 50 to 1000 nanometers, and wherein collagen is not cross-linked through the particles, and wherein the particles comprise ceramic material, biodegradable material, or metallic material of gold, silver, platinum, titanium, nickel, or copper.

2. The composition of claim 1, wherein the collagen is cross-linked through the collagen.

3. The composition of claim 2, wherein the cross-linked collagen is porous and has an average pore size ranging from 500 nanometers to 200 micrometers or from 1 micrometer to 100 micrometers.

4. The composition of claim 2, wherein the collagen is cross-linked with a carbodiimide cross-linking agent.

5. The composition of claim 1, wherein the particles have an average particle diameter between 50 and 150 nanometers.

6. The composition of claim 1, wherein the amine reactive groups are mercapto ethyl amine or cystamine or both.

7. The composition of claim 1, wherein the ratio of particles to collagen is a range of $1 \times 10^9$ particles per mg of collagen to $2 \times 10^{10}$ particles per mg of collagen.

8. The composition of claim 1, further comprising embryonic stem cells, adult stem cells, induced pluripotent stem cells, epithelial cells, exocrine or endocrine cells, myoblasts, fibroblasts, osteoblasts, chondroblasts, stromal cells, hepatocytes, islet cells, neuroblasts, keratinocytes, osteoclasts, osteocytes, cardiac cells, chondrocytes, endothelial cells, or muscle cells, or any combination thereof.

9. The composition of claim 1, wherein the composition is a gel, solution, paste, or dehydrated rigid structure.

10. The composition of claim 1, wherein the composition is comprised in a syringe.

11. The composition of claim 1, wherein the composition is a dermal or epidermal skin-equivalent.

12. The composition of claim 1, wherein 15 to 20% of the free carboxylic acid groups of the collagen are covalently bound to the particles through an amide bond.

13. A method for bulking articular cartilage by increasing tissue volume in a person, comprising administering to a person in need thereof the composition of claim 1, wherein the composition is administered by injection into a joint capsule.

14. The method of claim 13, wherein the collagen is cross-linked and porous and has an average pore size ranging from 500 nanometers to 200 micrometers.

15. The method of claim 14, wherein the particles have an average particle diameter between 50 and 150 nanometers.

16. The method of claim 13, wherein the reactive group is mercapto ethyl amine or cystamine or both.

17. The method of claim 13, wherein the ratio of particles to collagen is a range of $1 \times 10^9$ particles per 1 mg of collagen to $2 \times 10^{10}$ particles per 1 mg of collagen.

18. The method of claim 13, wherein the composition is a gel, solution, paste, or dehydrated rigid structure.

19. The method of claim 13, wherein 15 to 20% of the free carboxylic acid groups of the collagen are covalently bound to the particles through an amide bond.

20. The method of claim 13, wherein 2 to 4 mg of a carbodiimide cross-linking agent per 30 mg of collagen is used to form the covalent bonds.

21. The method of claim 13, wherein 0.5 to 0.2 mg of a carbodiimide cross-linking agent per $1 \times 10^9$-$2 \times 10^{10}$ particles is used to form the covalent bonds.

22. A method for filling voids, defects, or increasing tissue volume in a person, comprising administering to a person in need thereof the composition of claim 1, wherein the composition is administered by intradermal or subcutaneous injection.

23. The method of claim 22, wherein the void is a facial fine line, wrinkle, crease, pit, or nodule, and wherein the appearance of the facial fine line, wrinkle, crease, pit, or nodule is reduced after administration of the composition.

24. The method of claim 22, wherein the composition is administered to a person's lip, and wherein the volume of the lip is increased after administration of the composition.

25. The composition of claim 1, wherein the covalent amide bonds are formed between free carboxylic acid groups of isolated or purified soluble collagen and amine reactive groups of the particles.

26. The composition of claim 1, wherein the collagen is injectible.

27. The composition of claim 1, wherein the collagen is soluble.

28. The composition of claim 1, wherein the collagen is not electrospun.

* * * * *

UNITED STATES PATENT AND TRADEMARK OFFICE
CERTIFICATE OF CORRECTION

PATENT NO.        : 9,827,323 B2
APPLICATION NO.   : 13/155111
DATED             : November 28, 2017
INVENTOR(S)       : Anthony Harris et al.

It is certified that error appears in the above-identified patent and that said Letters Patent is hereby corrected as shown below:

On the Title Page

Item (75), Inventors, Line 2:
Delete "Johnathan" and replace with -- Jonathan --.

Signed and Sealed this
Third Day of April, 2018

Andrei Iancu
*Director of the United States Patent and Trademark Office*